(12) United States Patent
Kazlow et al.

(10) Patent No.: US 10,182,936 B2
(45) Date of Patent: *Jan. 22, 2019

(54) FOOT AILMENT SUPPORT AND CUSHION APPARATUS

(71) Applicants: Terence Kazlow, Webster, NY (US); Michael G. Lyons, Hernando, MS (US)

(72) Inventors: Terence Kazlow, Webster, NY (US); Michael G. Lyons, Hernando, MS (US)

(73) Assignee: Smart Medical Suppliers Inc, Webster, NY (US)

(*) Notice: Subject to any disclaimer, the term of this patent is extended or adjusted under 35 U.S.C. 154(b) by 948 days.

This patent is subject to a terminal disclaimer.

(21) Appl. No.: 14/214,849

(22) Filed: Mar. 15, 2014

(65) Prior Publication Data

US 2014/0343474 A1    Nov. 20, 2014

Related U.S. Application Data

(63) Continuation-in-part of application No. 13/897,029, filed on May 17, 2013, now abandoned.

(60) Provisional application No. 61/648,829, filed on May 18, 2012.

(51) Int. Cl.
*A61F 5/01* (2006.01)

(52) U.S. Cl.
CPC .................. *A61F 5/0111* (2013.01)

(58) Field of Classification Search
CPC .... A61F 5/0111; A61F 5/0113; A61F 5/0127; A61F 5/0195; A61F 5/32; A61F 5/34
USPC .............................. 602/27, 65, 66
See application file for complete search history.

(56) References Cited

U.S. PATENT DOCUMENTS

| | | | |
|---|---|---|---|
| 2,708,930 A * | 5/1955 | Lowman | A61F 13/065 602/27 |
| 3,506,000 A | 4/1970 | Baker et al. | |
| 4,409,976 A * | 10/1983 | Pence | A61F 13/066 602/65 |
| 5,135,473 A * | 8/1992 | Epler | A61F 13/066 2/22 |
| 6,379,321 B2 | 4/2002 | Gaylord et al. | |
| 7,018,351 B1 * | 3/2006 | Iglesias | A61F 5/0111 128/882 |
| 7,022,096 B1 * | 4/2006 | Alfieri | A63B 71/1225 602/23 |

(Continued)

OTHER PUBLICATIONS

Page 2 of Velcro High Technology Hook (HTH) Sales Brochure, Velcro, Manchester, NH, US.
Page 8 of Fastenation Product Brochure, Clifton, NJ, US.

*Primary Examiner* — Kari Rodriquez
(74) *Attorney, Agent, or Firm* — Tracy Jong Law Firm; Tracy P. Jong; Cheng Ning Jong (57) ABSTRACT

A foot ailment support and cushion apparatus configured for supporting an ankle and a plantar on a foot. The apparatus comprises an ankle strap and a plantar strap assembly. The ankle strap comprises a generally curvilinear band having an inner surface, an outer surface, two longitudinal ends, a minor edge, a major edge, a notch and an attaching means disposed on one of the two longitudinal ends, where the inner surface is oppositely disposed from the outer surface, the minor edge connects to the major edge at the two longitudinal ends of the band and the notch is disposed along a portion of the major edge. The plantar strap assembly includes two attachment ends and an elastic strap.

15 Claims, 10 Drawing Sheets

(56) References Cited

U.S. PATENT DOCUMENTS

2008/0154166 A1\* 6/2008 Beckwith .............. A61F 5/0113
602/27

\* cited by examiner

FOOT AILMENT SUPPORT AND CUSHION APPARATUS

PRIORITY CLAIM AND RELATED APPLICATIONS

This continuation-in-part application claims priority to provisional application U.S. Ser. No. 61/648,829 filed May 18, 2012 and non-provisional application U.S. Ser. No. 13/897,029 filed May 17, 2013. Each of said applications is incorporated by reference herein in its entirety.

BACKGROUND OF THE INVENTION

1. The Field of the Invention

The present invention is directed generally to an apparatus for supporting a portion of the human foot. More specifically, the present invention is directed to an apparatus disposed in a configuration suitable for supporting a foot experiencing various foot ailments, such as Achilles tendonitis, plantar fasciitis, ankle contusion, heel pain and heel spur.

2. Background Art

Many foot splints and braces have been devised to alleviate various foot ailments caused by sprained ankle, "fallen arches," plantar fasciitis, heel spurs, injured heel and the like. Such devices are typically bulky and used to replace the normal footwear of the wearer, e.g., a shoe. Ankle straps, woven fabrics and other less intrusive devices have also been devised to allow the wearer of such devices to put on his or her footwear upon putting on such devices. However, a device such as one disclosed below, although capable of being disposed around an ankle, does not solve several critical needs associated with the various typical foot ailments.

U.S. Pat. No. 6,379,321 to Gaylord et al. (hereinafter Gaylord) discloses a plantar fasciitis foot support apparatus, including a support strap for being positioned in a generally U-shaped configuration along the medial and lateral aspects of the ankle and extending under and supporting the plantar fascia region of the foot. An ankle-encircling retention strap is attached by its opposite ends to the support strap at a substantially right angle thereto for retaining the support strap in a supporting position against the plantar fascia region. The support strap includes an inelastic segment and at least one attached elastic segment for providing controlled stretch of the support strap during placement on the foot and during subsequent movement of the foot while the support is in place. Complementary and releasably-adjustable fastener elements are carried by the retention strap and the support strap for permitting lengthwise adjustment of the support strap relative to the plantar fascia region of the foot. The fastener elements include a first fastener element carried by an outer surface of the retention strap, a second fastener element carried by an inner surface of the support strap for being adjustably-mated with the first fastener element for retaining the support strap and the retention strap in a desired position relative to each other, and a third fastener element carried on an outer surface of the support strap. A fastener cover is carried by the retention strap and has a fourth fastener element carried on an inner surface thereof for mating with the third fastener element of the support strap. This patent discloses a retention strap that is fabricated of a strap having a constant width and therefore not configured for snug fit, suitable contour and sufficient support for the ankle.

U.S. Pat. No. 3,506,000 to Baker et al. discloses an ankle support comprising a body member to extend about the Achilles tendon at the back of the foot and along the inside and outside of the foot with a band at its upper edge to support it in position and with stretchable straps supported in position to the body member and extending in opposite directions, the straps being of a length to pass under the arch of the foot and over instep in opposite directions one from the other and then about the leg in opposite directions so as to overlap with means to hold them in overlapping position. This patent also discloses an ankle support having a band and straps of constant width. This design is not configured for snug fit, suitable contour and sufficient support for the ankle. In addition, the apparatus is not intuitive to apply as the apparatus is composed of a pair of wings attached to a band and straps where the straps are passed under the plantar fascia and secured to the heel region.

Thus, there arises a need for a device for supporting and cushioning a foot experiencing common foot ailments where the device is simple and economical in construction while also being simple and intuitive to use.

SUMMARY OF THE INVENTION

The present invention is directed toward a foot ailment support and cushion apparatus configured for supporting an ankle and a plantar fascia of a foot. The apparatus comprises an ankle strap and a plantar strap assembly. The ankle strap comprises a generally curvilinear band having an inner surface, an outer surface, two longitudinal ends, a minor edge, a major edge and a notch. The inner surface is opposingly disposed from the outer surface, the minor edge connects to the major edge at the two longitudinal ends of the curvilinear band and the notch is disposed along a portion of the major edge. The ankle strap further comprises an attaching means disposed on one of the two longitudinal ends. The plantar strap assembly includes two attachment ends and an elastic strap. In one embodiment, the width of the elastic strap is about 2 inches.

The curvilinear band is configured to be wrappable around the ankle such that the outer surface of the band faces away from the ankle and the attaching means of the ankle strap is removably secured to the outer surface of the band. In use, the band is configured to create sufficient pressure around the ankle to both aid in healing foot ailments (such as, for example, Achilles tendonitis, plantar fasciitis, ankle contusion, heel pain and heel spur) and serve as attachment points for the plantar strap assembly which applies pressure to the plantar fascia when installed. The plantar strap assembly is configured to be disposed such that the elastic strap is disposed along the medial and lateral aspects under the bottom of the foot, engaging the plantar fascia region of the foot and each of the two attachment ends is removably attached to a portion of the outer surface of the band.

The attaching means comprises at least one hook strap extending outwardly from one of the two longitudinal ends of the band.

The inner surface is fabricated of a breathable washable antimicrobial moisture wicking mesh material comprising polyester or nylon.

The outer surface is fabricated of a material comprising polyester or nylon and configured for removable attachment with the attaching means of the band and the two attachment ends of the plantar strap.

The plantar strap assembly is provided for being positioned in a generally U-shaped configuration along the medial and lateral aspects of the ankle and extending under and supporting the plantar fascia region of the foot. The ankle-encircling ankle strap is attached by its opposite ends to the plantar strap assembly at a substantially right angle thereto for retaining the plantar strap assembly in a supporting position against the plantar fascia region. In one embodiment, the apparatus further comprises a gelatin pack disposed around the notch on the major edge of the band. The notch is configured for engaging the heel region of the foot. The gelatin pack also comprises at least two gelatin-filled compartments for more evenly distributing the gel contents of the gelatin pack.

Accordingly, it is a primary object of the present invention to provide a foot ailment support and cushion apparatus which is lightweight and comfortable within conventional footwear.

It is another object of the present invention to provide a foot ailment support and cushion apparatus, wherein the plantar strap assembly including the attachment ends is fabricated of non-intrusive, thin and durable materials, thereby permitting the use of such apparatus within conventional footwear.

It is another object of the present invention to provide an ankle strap suitably configured to straddle the Achilles tendon for secure attachment of the ankle strap to the ankle.

Whereas there may be many embodiments of the present invention, each embodiment may meet one or more of the foregoing recited objects in any combination. It is not intended that each embodiment will necessarily meet each objective. Thus, having broadly outlined the more important features of the present invention in order that the detailed description thereof may be better understood, and that the present contribution to the art may be better appreciated, there are, of course, additional features of the present invention that will be described herein and will form a part of the subject matter of this specification.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

PARTS LIST

2—foot ailment support and cushion apparatus
3—ankle strap
4—band
6—attaching means
8—hook strap
9—loop attachment end
10—fringe
12—notch
14—stitching
16—inner surface
17—outer surface
18—angle between two hook straps
20—width of band
21—minor edge
22—length of minor edge of band
23—major edge
24—perimeter length of short portion of minor edge
25—perimeter length of long portion of minor edge
26—angle between centrally disposed line in notch and major projected edge
27—distance between the longitudinal end on which the hook strap is affixed to the band and the point at which the two lines extending from longitudinal ends of band, meet 28—angle between longitudinal ends of band
29—distance between the opposing longitudinal end on which the hook straps are affixed to the band and the point at which the two lines extending from longitudinal ends of band, meet
30—plantar strap assembly
31—centrally disposed line in notch
32—elastic strap
34—elastic strap attachment end
36—stitching securing elastic strap attachment end to elastic straps
38—micro hooks
40—cavity between two stacked elastic straps
42—plantar gelatin pack
44—gelatin
46—compartment wall of gelatin pack
48—heel gelatin pack
50—right foot
52—left foot
54—cushioned ankle band
56—cushioned ankle strap
58—shoe
60—ankle
62—heel
64—plantar fascia
66—edge of gelatin pack
68—Achilles tendon
70—elastic strap
72—conventional ankle strap
74—conventional plantar strap assembly
76—width of elastic strap
78—length of plantar strap assembly
80—plantar strap assembly
82—width of elastic straps 32
84—length of plantar strap assembly Particular Advantages of the Invention The present apparatus provides suitable support and cushioning to the plantar fascia region and Achilles heel region of a foot. Cushioning on plantar fascia is provided by the elastic straps of the plantar strap assemblies. Cushioning on Achilles heel is provided by both (1) the curvilinear band which provides firm and evenly distributed pressure over the ankle and Achilles heel regions and in one embodiment and (2) a second gelatin pack disposed around (or in the vicinity of) a notch in the band, wherein the notch is lodged against the heel region and such that the band is positioned with the second gelatin pack pressed firmly against the heel region.

Upon securing the band to an ankle, the curvilinear nature of the band causes the band to be snugly fitted on the ankle, i.e., the inner surface exerts substantially uniform pressure on the ankle. In contrast, Gaylord discloses a rectilinear retention strap that is incapable of snug fit to the ankle. Gaylord's apparatus is therefore unsuitable for providing cushion and support for Achilles tendonitis, ankle contusion, heel pain and heel spur or any foot regions related to the heel and ankle.

The present apparatus is agnostic in terms of which foot it is configured to be placed on as the apparatus is capable of being configured to apply support and cushioning to the ankle, heel and plantar fascia regions of either left or right foot.

DETAILED DESCRIPTION OF A PREFERRED EMBODIMENT

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

Figure 1:
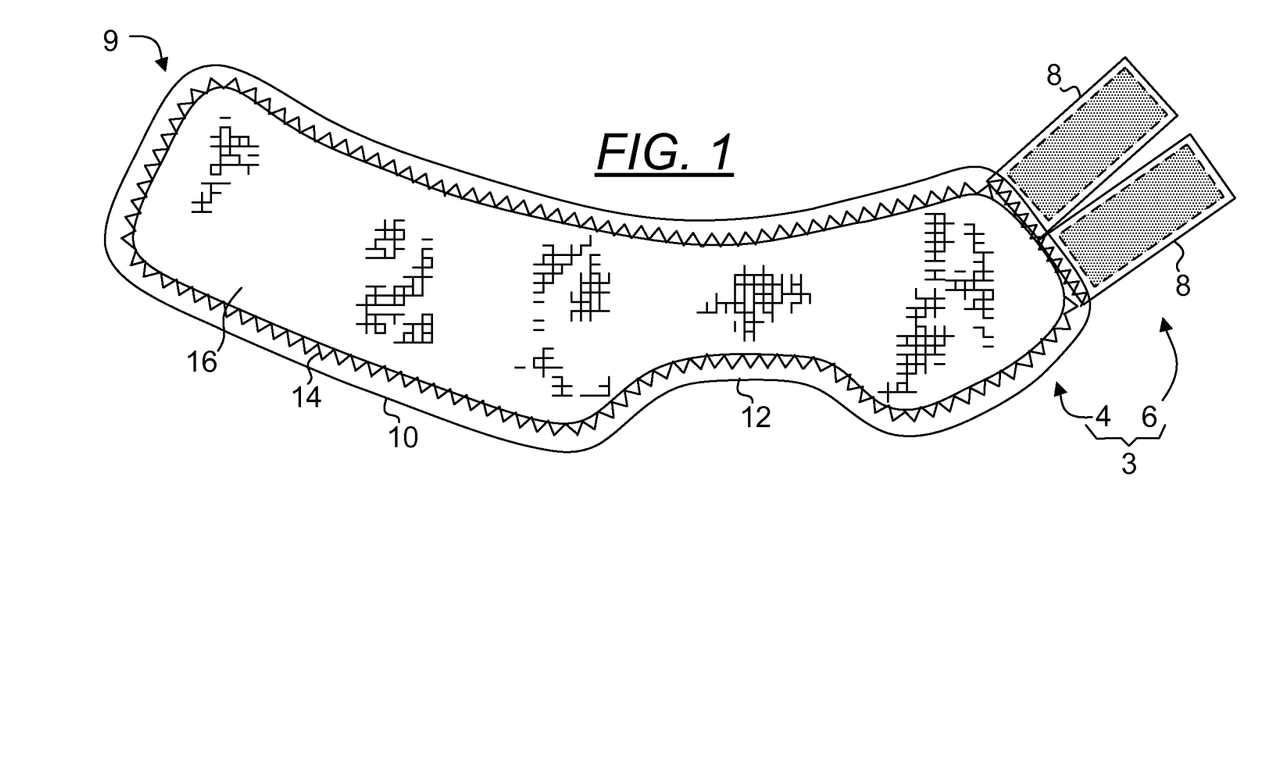
FIG. 1 is a front orthogonal view of an ankle strap according to one embodiment of the present invention.
Figure 2:
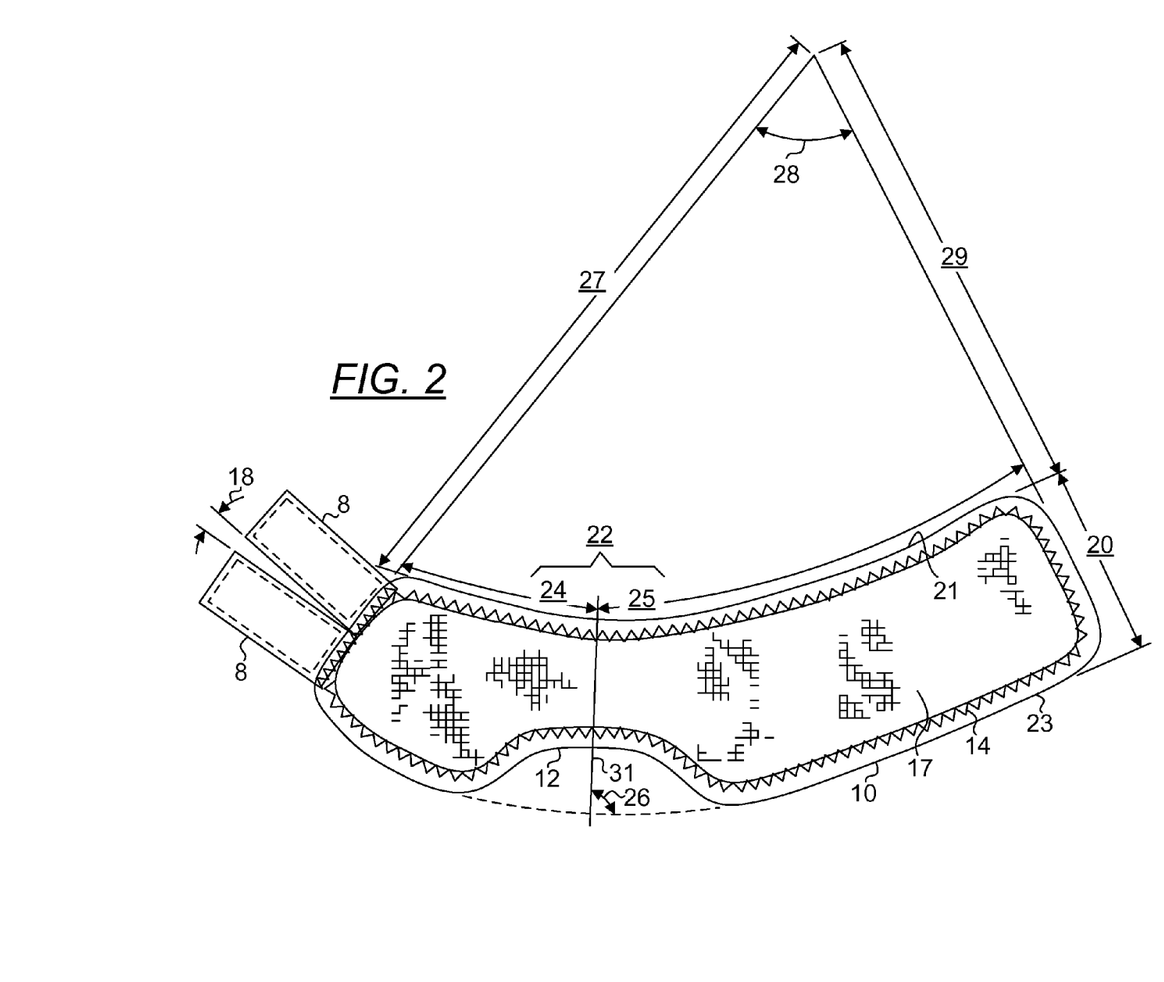
FIG. 2 is a rear orthogonal view of an ankle strap according to one embodiment of the present invention.

FIGS. 1 and 2 are front and rear orthogonal views, respectively, of an ankle strap 3 according to one embodiment of the present invention. The ankle strap 3 comprises a generally curvilinear band 4 having an inner surface 16, an outer surface 17, two longitudinal ends, a minor edge 21, a major edge 23, and a notch 12. The inner surface 16 is opposingly disposed from the outer surface 17 while the minor edge 21 connects to the major edge 23 at the two longitudinal ends of the curvilinear band 4 and the notch 12 is disposed along a portion of the major edge 23. The ankle strap 3 further comprises an attaching means 6 disposed on one of its two longitudinal ends. In one embodiment, the attaching means comprises a pair of hook straps 8 extending outwardly from one of the two longitudinal ends. Applicant discovered that by disposing hooks on the hook straps 8 where the hooks are mated with loops disposed on the outer surface 17 of band 4, any such hooks are protected from inadvertent engagement with any materials such as fabrics from socks and trousers, etc. An additional cover for protecting such hooks is thereby rendered unnecessary. The hook straps 8 are configured to diverge at an angle 18 of about 10 degrees from one another as they extend from one of the two longitudinal ends.

The band 4 is curvilinear in shape and includes substantially the same width across its entire length. The shape of the band can be defined more specifically in the following ways. The orientation of the longitudinal ends of the band 4 is defined by two lines, each extending from a longitudinal end of the band 4 and intersects to make angle 28, for example, of about 74 degrees. Length 27, i.e., the distance between the longitudinal end on which the hook straps 8 are affixed to the band 4 and the point at which the two lines extending from longitudinal ends meet, measures about 8-13/16 inches. Length 29, i.e., the distance between the opposing end of band 4 on which the hook straps 8 are affixed to the band 4 and the point at which the two lines extending from the longitudinal ends of the band, meet. Length 29 measures about 7⅞ inches. In order to more specifically locate the notch 12, a line 31 centrally disposed in the notch 12 is drawn to divide the notch 12 in half, resulting in perimeter length 24 of about 3.5 inches and perimeter length 25 of about 7⅛ inches where length 22 is the perimeter length of the minor edge. The width 20 of band 4 measures about 3 inches. Angle 26 is an angle line 31 makes with the major edge 23 of the band 4 and this angle is substantially a right angle. Each hook strap 8 comprises hooks disposed on the surface configured for removable attachment with loops of the outer surface 17. Each hook strap 8 is attached to the band 4, for example, by sewing stitches 14, to the band 4. Although less desirable for reasons previously disclosed, loops may alternatively be disposed on the hook straps and hooks on the outer surface 17 of the band 4 to cause removable engagement of the hook straps on the outer surface 17 of the band 4.

The ankle strap 3 is suitably configured to straddle the Achilles tendon 68 (shown in FIGS. 9 and 13) for secure attachment of the ankle strap 3 to the ankle. In use, the notch 12 is aligned with the Achilles tendon 68 such that when tightened, the band materials on the outer edges of the notch 12 prevent the band 4 from rotation with respect to the ankle.

The curvilinear band 4 is configured to be wrappable around an ankle such that the outer surface 17 faces away from the ankle 60 and attaching means is removably secured to the outer surface 17 of the band. In use, the band 4 is encircled around an ankle and proper pressure around the ankle is maintained by lapping one end of the band 4 over the other and securing the overlap by pressing the hook straps 8 against band 4. The band 4 therefore both (1) aids in healing Achilles tendonitis, plantar fasciitis, ankle contusion, heel pain and heel spur and (2) serves as attachment points for the plantar strap assembly 30 which applies proper pressure to the plantar fascia 64 when installed.

Figure 3:
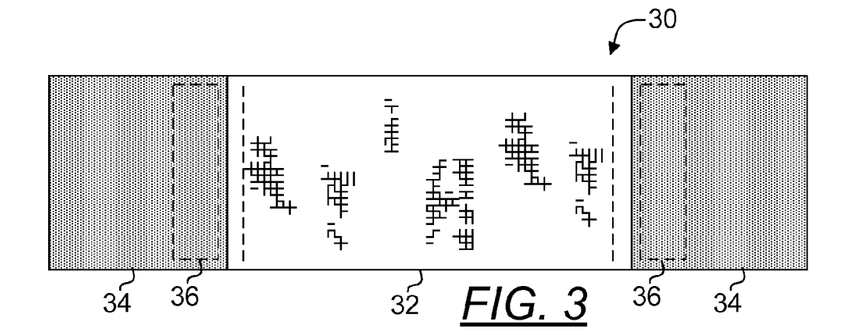
FIG. 3 is a front orthogonal view of a plantar strap according to the present invention.
Figure 4:
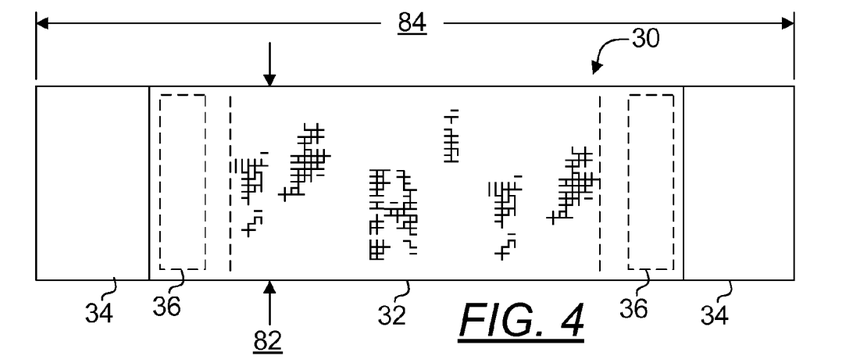
FIG. 4 is a rear orthogonal view of a plantar strap according to the present invention.
Figure 5:
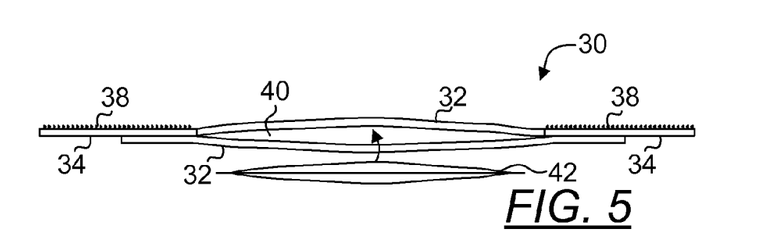
FIG. 5 is a side orthogonal view of a plantar strap and plantar gelatin pack aligned for insertion into the cavity between two elastic straps.
Figure 6:
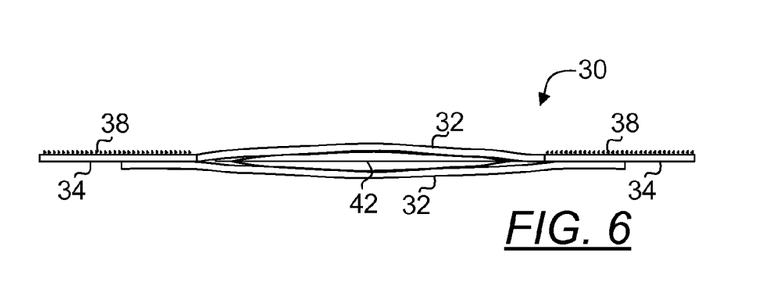
FIG. 6 is the view of FIG. 5 depicting the plantar gelatin pack already inserted into the cavity between the two elastic straps.
Figure 7:
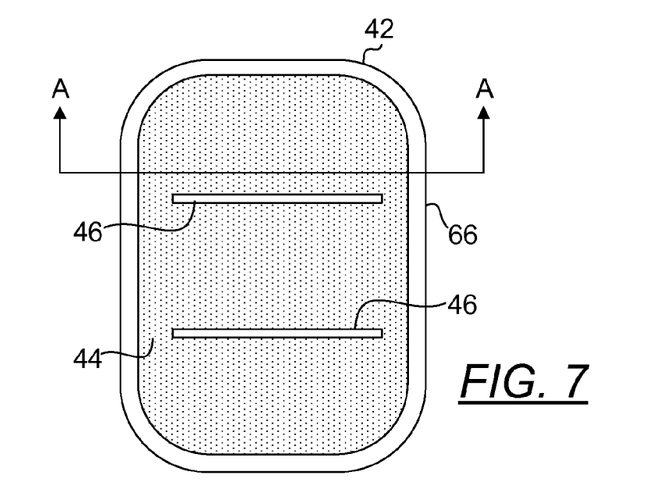
FIG. 7 is a front orthogonal view of an exemplary gelatin pack as used in the present invention.
Figure 8:
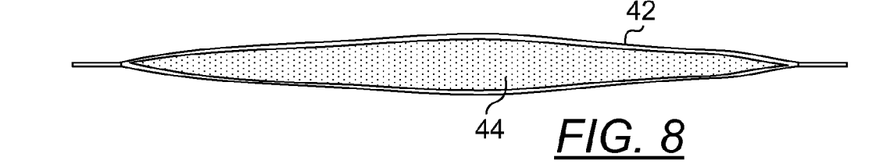
FIG. 8 is a side orthogonal sectional view of the gelatin pack of FIG. 7.

FIGS. 3 and 4 are front and rear orthogonal views, respectively, of a plantar strap assembly 30 according to the present invention. FIG. 5 is a side orthogonal view of a plantar strap and plantar gelatin pack aligned for insertion into the cavity between two elastic straps 32. FIG. 6 is similar to the view of FIG. 5, depicting the plantar gelatin pack already inserted into the cavity between the two elastic straps 32. FIG. 7 is a front orthogonal view of an exemplary gelatin pack as used in the present invention. FIG. 8 is a side orthogonal sectional view of the gelatin pack of FIG. 7. The present apparatus further comprises a plantar strap assembly 30 having two attachment ends 34 and two stacked elastic straps 32, each including two longitudinal ends. The two stacked elastic straps 32 are fixedly attached at their longitudinal ends, each attachment end is fixedly secured to one of the two longitudinal ends and a cavity is formed between the two stacked elastic straps 32. The plantar strap assembly 30 is configured to be disposed such that the two stacked elastic straps 32 are disposed along the medial aspect under the bottom of the foot engaging the plantar fascia 64 region of the foot. In use, each of the two attachment ends 34 is removably attached to a portion of outer surface 17 of the curvilinear band 4. In one embodiment, the width 82 of each of the stacked straps 32 and the length 78 of the plantar strap assembly 80 measures about 2 inches and from about 7-¼ to about 8 inches, respectively, when the elastic strap 32 is in its unstretched condition. In one embodiment, each of the stacked straps 32 is constructed from a highly resistant woven-elastic bungee material and capable of preventing sliding and shifting of the elastic straps 32 when its wearer strides.

The apparatus further comprises a gelatin pack 42 disposed within the cavity 40 to further cushion the bottom of a foot. The gelatin pack 42 comprises at least two gelatin-filled compartments for more evenly distributing the gelatin contents 44 of the gelatin pack. In one embodiment, the gelatin pack 42 is fabricated by stamping a composite plastic-gelatin-plastic layer where the plastic layers are disposed in their molten state resulting in a thin pack having an edge 66 and at least one compartment wall 46. Each compartment wall 46 extends partially over a major dimension of the gelatin pack 42, leaving the gelatin contents 44 to freely flow between compartments to provide suitable cushioning and resilience. In addition to providing comfort, the gelatin pack serves as a thermal reservoir for thermal treatment to the plantar fascia. Each gelatin pack includes a gelatin contained in a relatively planar and thin plastic container which can be safely and easily placed in a freezer for lowering its temperature. If desired, a gelatin pack may alternatively be placed in a microwave oven for raising its temperature. The gelatin contained within the gelatin pack is preferably a material having sufficient thermal mass to ensure prolonged cold or heat treatment to reduce symptoms associated with the foot ailments disclosed herein.

The outer surface 17 is configured for removable attachment with the attaching means of the ankle strap 3 and the two attachment ends of the plantar strap assembly 30 and the outer surface 17 is fabricated of a material comprising loops. Such surface is typically woven or knitted with terry loops on the faces of the fabric, and are designed specifically to serve as the female, loop part of conventional hook-and-loop fastening elements.

The inner surface is fabricated of a breathable washable antimicrobial moisture wicking mesh material comprising polyester or nylon. The inner and outer surfaces 16, 17 are secured at their edges by, for example, sewing a fringe 10.

Figure 9:
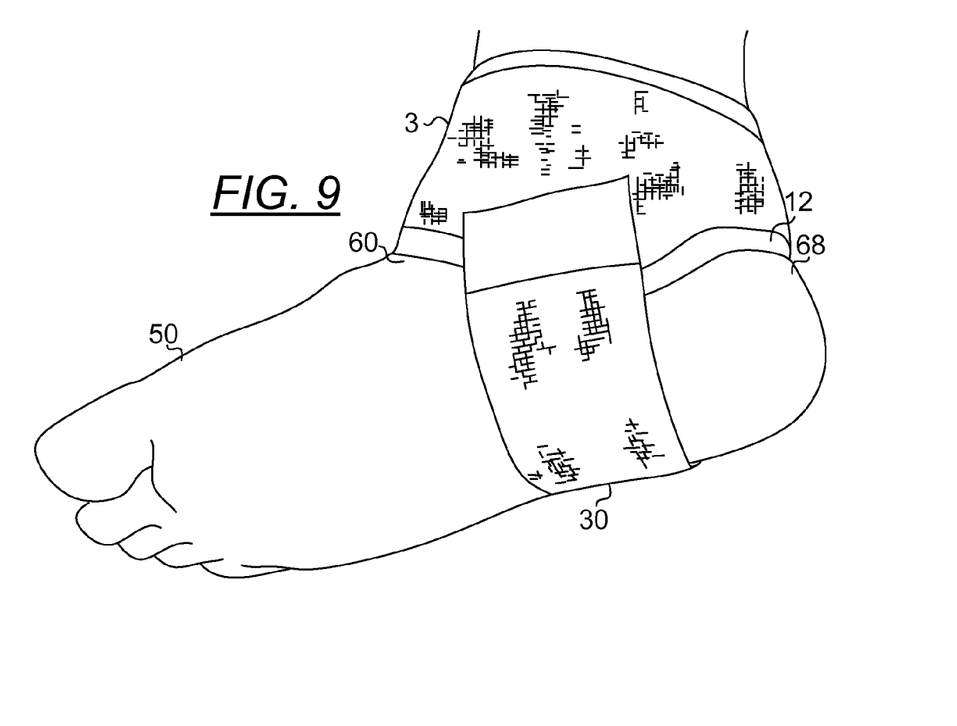
FIG. 9 is a bottom perspective view depicting a configuration with which a foot ailment support and cushion apparatus is applied to a right foot.
Figure 10:
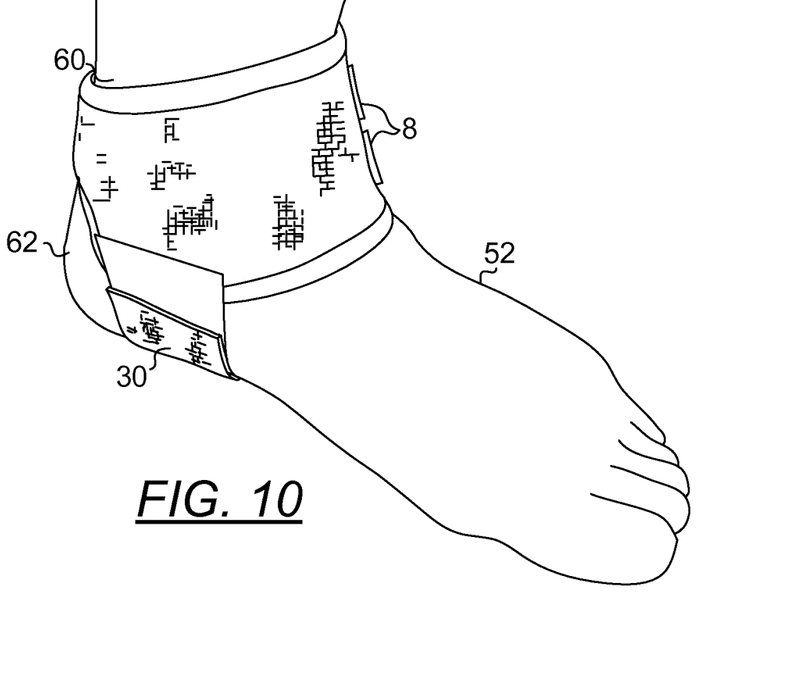
FIG. 10 is a top front perspective view depicting a configuration with which a foot ailment support and cushion apparatus is applied to a left foot.
Figure 11:
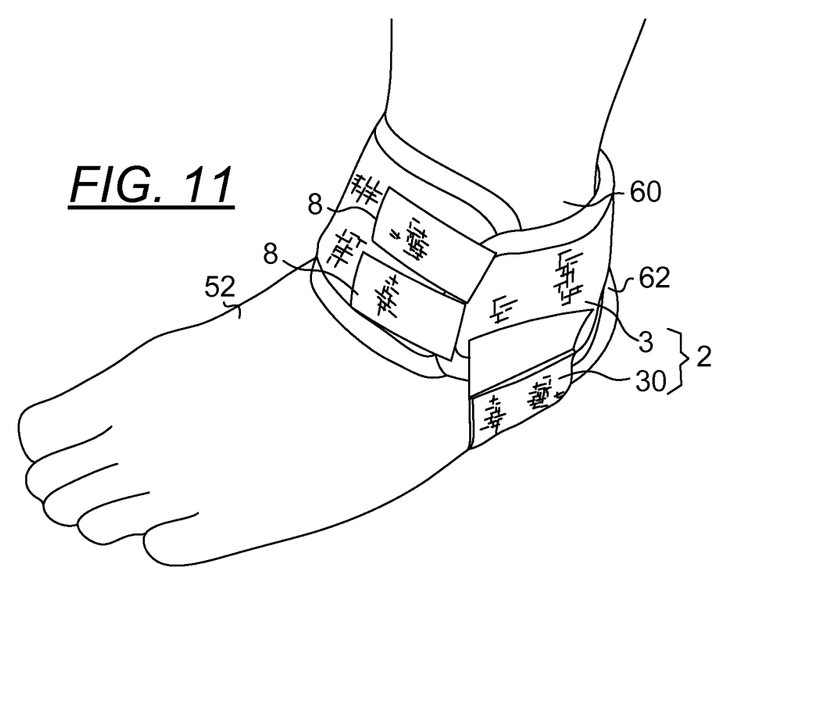
FIG. 11 is another top front perspective view depicting a configuration with which a foot ailment support and cushion apparatus is applied to a left foot.

FIG. 9 is a bottom perspective view depicting a configuration with which a foot ailment support and cushion apparatus is applied to a right foot 50. FIG. 10 is a top front perspective view depicting a configuration with which a foot ailment support and cushion apparatus is applied to a left foot 52. FIG. 11 is another top front perspective view depicting a configuration with which a foot ailment support and cushion apparatus is applied to a left foot. According to one embodiment of the invention, the plantar strap assembly 30 is provided for being positioned in a generally U-shaped configuration along the medial and lateral aspects of the ankle and extending under and supporting the plantar fascia 64 region of the foot. The ankle-encircling ankle strap 3 is attached by its opposite ends to the plantar strap assembly 30 at a substantially right angle thereto for retaining the plantar strap assembly 30 in a supporting position against the plantar fascia region. As the plantar strap assembly 30 is constructed as an independent unit from the ankle strap 3, each attachment end may be secured to the ankle strap 3 at different times or at about the same time. If the attachment ends are deployed at the same time, the elastic straps passed under the foot and each attachment end may be held with one hand until the elastic straps (disposed between the attachment ends) exert desired tension and hence proper pressure as a result to the plantar fascia before attachment ends get pressed onto the outer surface 17 of the band 4. Proper pressure is essential if the apparatus 2 is to perform its intended therapeutic functions. The plantar strap assembly may alternatively be attached at one attachment end to a portion of the outer surface 17 of the band 4 on one side of the ankle with one hand and the other attachment end is passed under the foot to the opposing side of the ankle and pressed against a portion of the outer surface 17 of the band 4. Each attachment end exerts a pull on the band 4 which comprises a shearing force against the hooks of the attachment end and the loops of the outer surface 17 at the point of connection between the band 4 and the plantar strap assembly 30.

Figure 12:
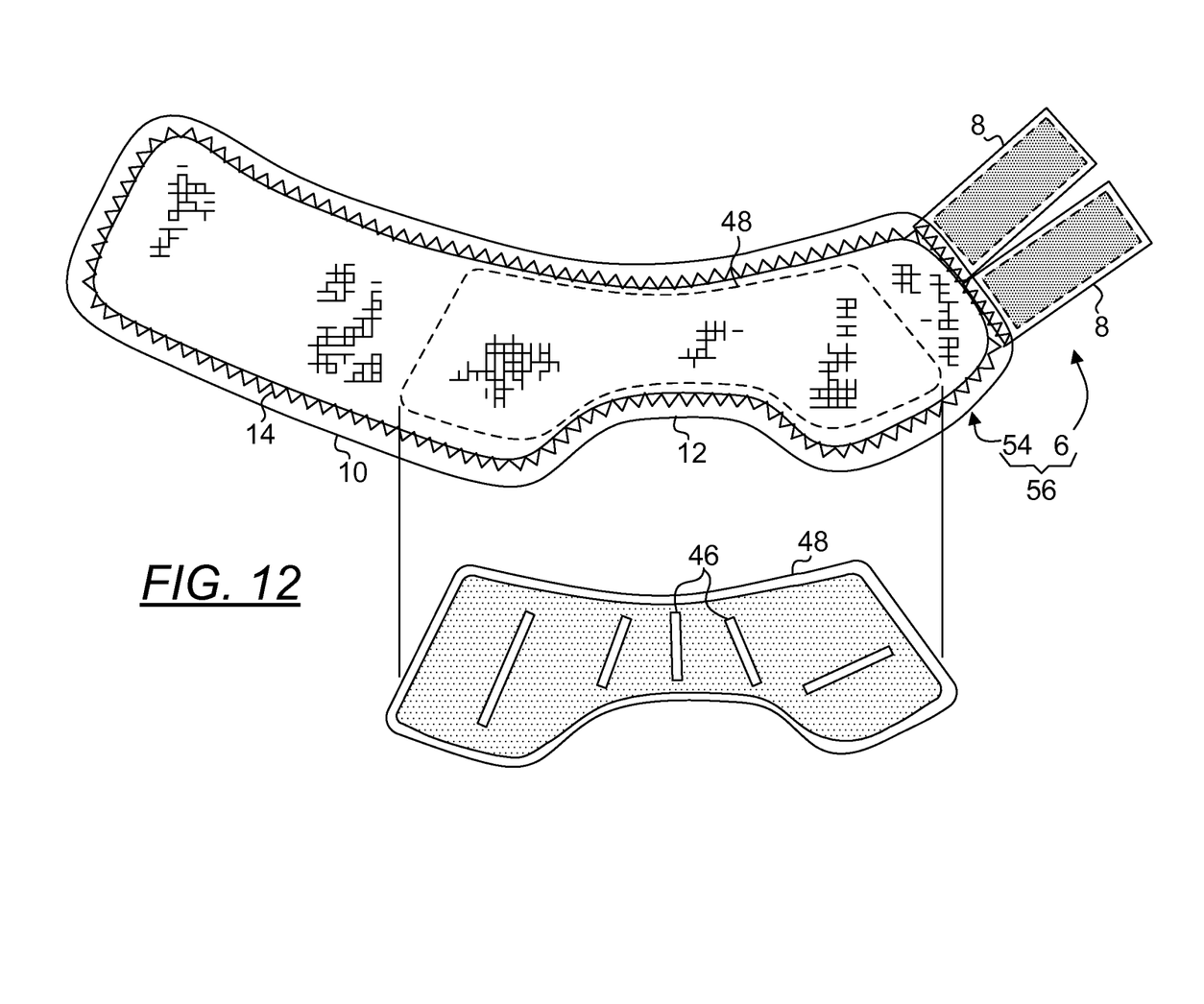
FIG. 12 is a front orthogonal view of a foot ailment support and cushion apparatus according to a second embodiment of the present invention.

FIG. 12 is a front orthogonal view of a foot ailment support and cushion apparatus according to a second embodiment of the present invention. The apparatus further comprises a second gelatin pack 48 disposed around the notch 12 on the major edge 23 in band 54 of ankle strap 56. The notch 12 is configured for engaging the heel 62 region of the foot. The second gelatin pack 48 also comprises at least two gelatin-filled compartments for more evenly distributing the gelatin contents of the second gelatin pack 48. The second gelatin pack 48 is similar to gelatin pack 42 except the second gelatin pack 48 is configured in a shape following the outline of the notch 12 and the immediate area surrounding the notch 12. In a preferred embodiment, the second gelatin pack 48 is disposed between the inner 16 and outer 17 surfaces and secured at a portion of its edge to one or both of the inner and outer surfaces.

Figure 13:
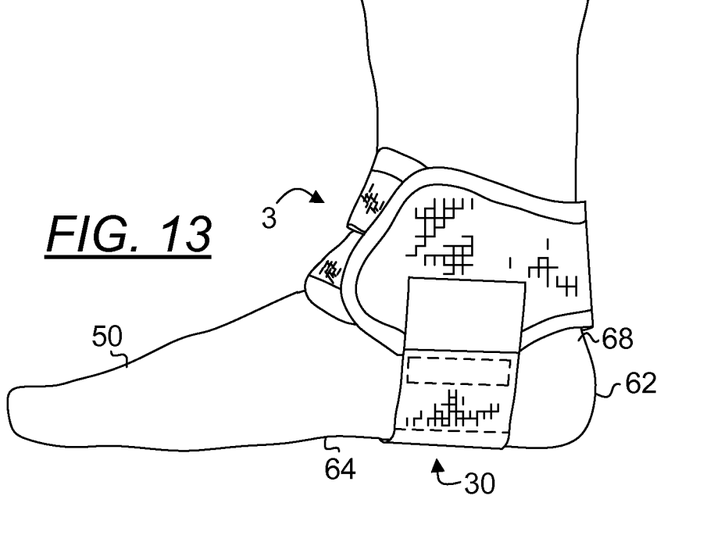
FIG. 13 is a side orthogonal view of a configuration with which a foot ailment support and cushion apparatus is applied to a right foot.
Figure 14:
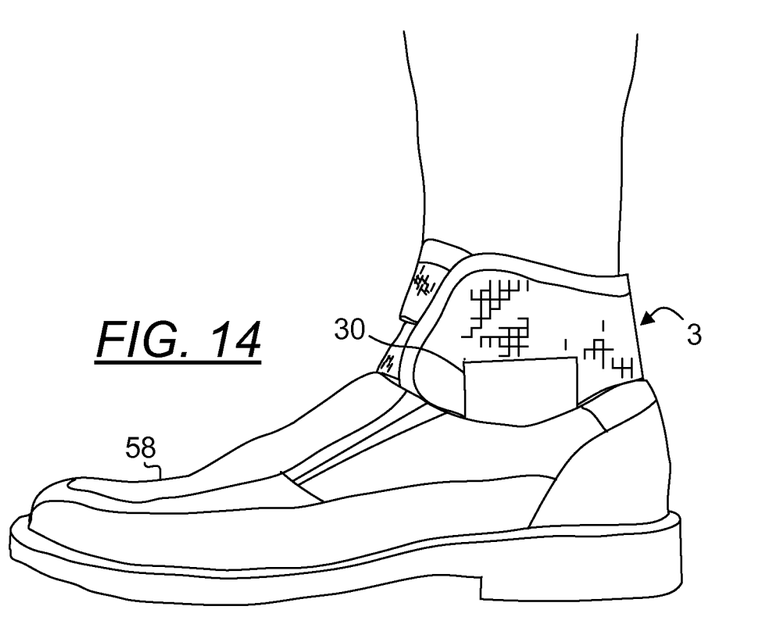
FIG. 14 is a side orthogonal view of a configuration depicting the present apparatus being worn by a user in cooperation with a shoe.

FIG. 13 is a side orthogonal view of a configuration with which a foot ailment support and cushion apparatus is applied to a right foot. FIG. 14 is a side orthogonal view of a configuration depicting the present apparatus being worn by a user in cooperation with a shoe 58. Accordingly, it is a primary object of the present invention to provide a foot ailment support and cushion apparatus which is lightweight and comfortable within conventional footwear. The plantar strap assembly 30 includes attachment ends which are fabricated of non-intrusive, thin and durable materials, thereby permitting the use of such apparatus within conventional footwear. In this embodiment, each attachment end is configured for removable engagement with the outer surface 17 and fabricated of a polymeric substrate or combination of polymeric and fabric substrate having micro hooks 38 disposed on one of its surfaces and fixedly attached to one end of the two stacked straps by, for example, sewing stitches 36. Examples of a suitable micro hook material include the hook portions of material High Technology Hook (HTH) 830 and 833 from VELCRO USA, Inc., Manchester, N.H. HTH 830 is made with a standard polypropylene resin while HTH 833 is made with a standard nylon resin. Both models afford a very low profile, suitable for applications where space is a concern such as on both sides of a plantar fascia.

As the present apparatus is fabricated of two separate pieces, i.e., the plantar strap assembly 30 and the ankle strap 3, the ankle strap 3 is capable of being used by itself. In contrast, Gaylord's retention and support straps are built as a single piece and the retention strap is fabricated of flimsy and unsuitably lightweight material which together make the retention strap unsuitable for aiding in relieving Achilles tendonitis, ankle contusion, heel pain and heel spur.

Figure 15:
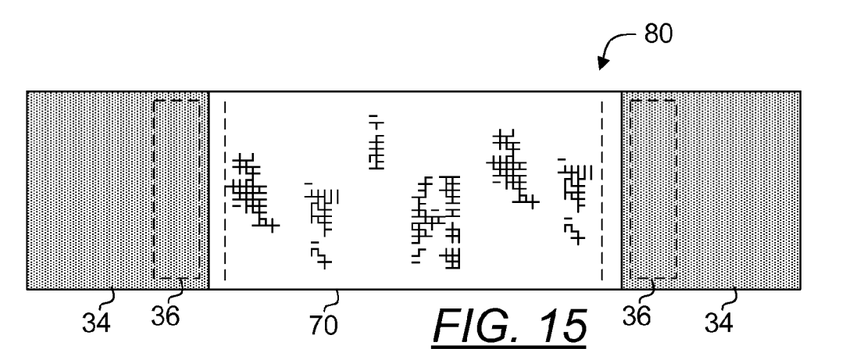
FIG. 15 is a front orthogonal view of another embodiment of a plantar strap according to the present invention.
Figure 16:
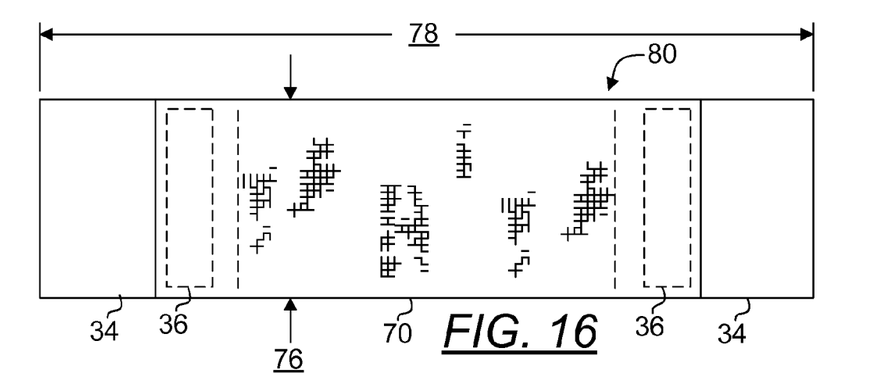
FIG. 16 is a rear orthogonal view of FIG. 15.
Figure 17:
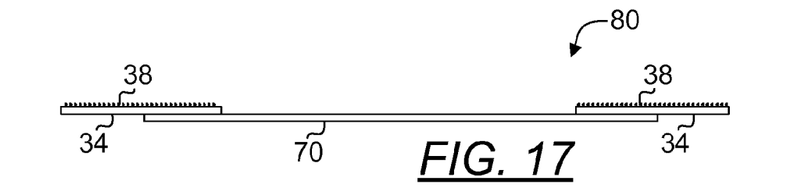
FIG. 17 is a side orthogonal view of FIG. 15.

FIG. 15 is a front orthogonal view of another embodiment of a plantar strap according to the present invention. FIG. 16 is a rear orthogonal view of FIG. 15. FIG. 17 is a side orthogonal view of FIG. 15. In cases where the use of a plantar gelatin pack 42 is deemed unnecessary, e.g., for prevention of initial on-set of, prevention of recurrence of, or during late stages of heeling of conditions such as Achilles tendonitis, ankle contusion, heel pain, heel spur as pain has subsided, a patient may choose to apply a plantar strap including a single elastic strap 70. In one embodiment, the width 76 of the elastic strap 70 and the length 78 of the plantar strap assembly 80 measures about 2 inches and from about 7-¼ to about 8 inches, respectively, when the elastic strap 70 is in its unstretched condition. In many circumstances, pain that occurs at the bottom of one's foot is not confined to one area and is considered dynamic and not static. In addition, pain is not typically felt consistently in one place in a narrow band, especially when a user is still mobile or active and uses his or her foot for daily activities, etc. Plantar fasciitis is an inflammation of the plantar fascia (the ligament under one's foot) from overuse, improper footwear, and/or being overweight. The fascia becomes inflamed due to micro fibers of the ligament tearing overtime. These tears create scar tissue which prevents the fibers from properly expanding and contracting adding to the pain. Repeated pressure placed on one's foot as experienced when one is taking a stride causes the micro fibers of the ligament to continue tearing. As these areas are typically not confined to a narrow band of about 1 or 1.5 inches wide, a present plantar strap is configured sufficiently wide to encompass such problem areas but not so wide that the plantar strap is cumbersome and presents a barrier for comfortable use. Plantar straps that are wider than about 3 inches are insufficiently flexible along their widths when disposed over a plantar fascia of a foot, making for uncomfortable fitting due to an excessive amount of materials over a plantar fascia region, especially when a footwear is disposed over the plantar fascia. In one embodiment, the elastic strap 70 is constructed from a highly resistant woven-elastic bungee material and capable of preventing sliding and shifting of elastic strap 70 when its wearer strides. An average wearer that is mobile while using the present apparatus may take as many as 1800 to 1900 steps per day and a sufficiently sturdy elastic strap 70 that is fabricated from the disclosed material maintains suitable pressure against the plantar fascia such that the elastic strap 70 provides relief while preventing any relative inadvertent displacement of the elastic strap 70 against the plantar fascia. The width 76 of the present elastic strap 70 offers a user increased stability and coverage across the bottom of their foot which not only addresses plantar fasciitis, but also prevents, treats and eliminates secondary conditions such as heel spurs and arch pain.

Figure 18:
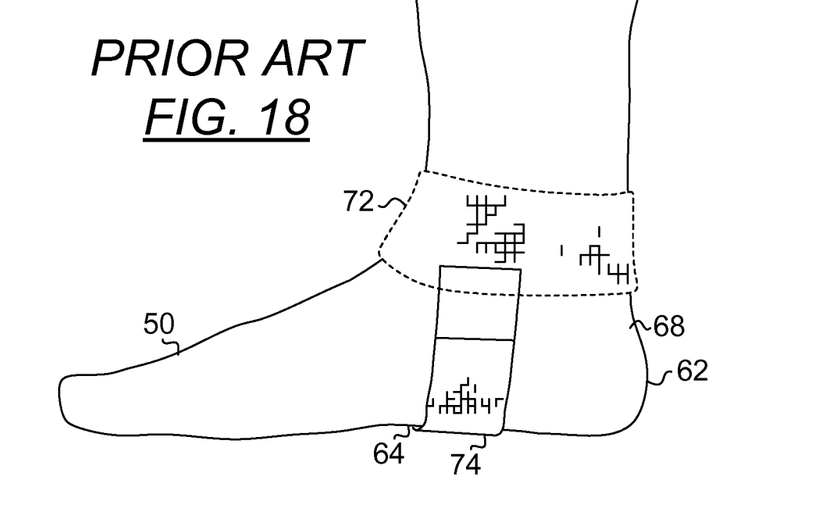
FIG. 18 is a view of another conventional of a plantar strap assembly disposed on a foot, depicting one example of the problems one may have with a conventional plantar strap assembly.
Figure 19:
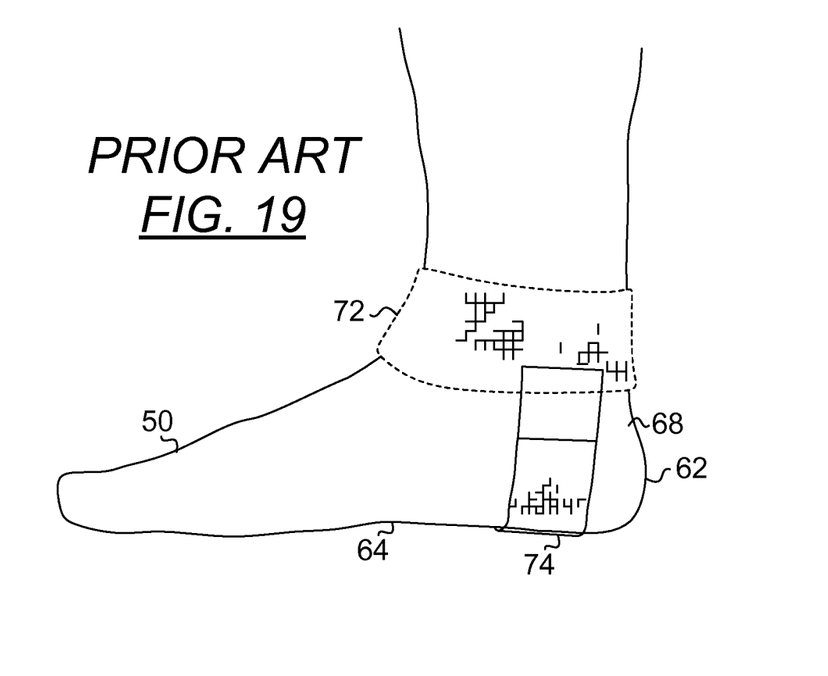
FIG. 19 is a view of another conventional of a plantar strap assembly disposed on a foot, depicting another example of the problems one may have with a conventional plantar strap assembly.

FIG. 18 is a view of another embodiment of a conventional plantar strap disposed on a foot, depicting one example of the problems one may have with a conventional plantar strap assembly. FIG. 19 is a view of another embodiment of a conventional plantar strap assembly disposed on a foot, depicting another example of the problems one may have with a conventional plantar strap assembly. The width of conventional straps typically ranges from about 1 inch to 1.5 inches. With such measurements, the decision to dispose a strap along a specific span of the plantar fascia can greatly affect the comfort and effectiveness of the strap on the foot. If the strap is disposed excessively forwardly on a foot as shown in FIG. 18, the strap is effective only for arch pain relief. If the strap is disposed excessively rearwardly on a foot, the strap is effective only for heel spur relief. If disposed between these two positions, the strap 74 is incapable of servicing one of the two areas of the foot. The plantar fascia is a broad structure of thick connective tissue that spans between the medial calcaneal tubercle (heel bone) and the proximal phalanges of the toes. The plantar fascia contributes to support of the arch of the foot by acting as a tie-rod, where it undergoes tension when the foot bears weight. Plantar fasciitis may lead to heel spurs, arch pain and other severe conditions. One biomechanical model estimated it carries as much as 14% of the total load of the foot. The width of the plantar strap assembly is therefore an important factor determining whether a plantar fasciitis can be properly treated or lessened. It shall also be noted that, due to the construction of the conventional ankle strap 72, it may not be sufficiently sturdy when a conventional strap 74 is coupled to the conventional ankle strap 72 to resist deformation.

Figures 20, 21:
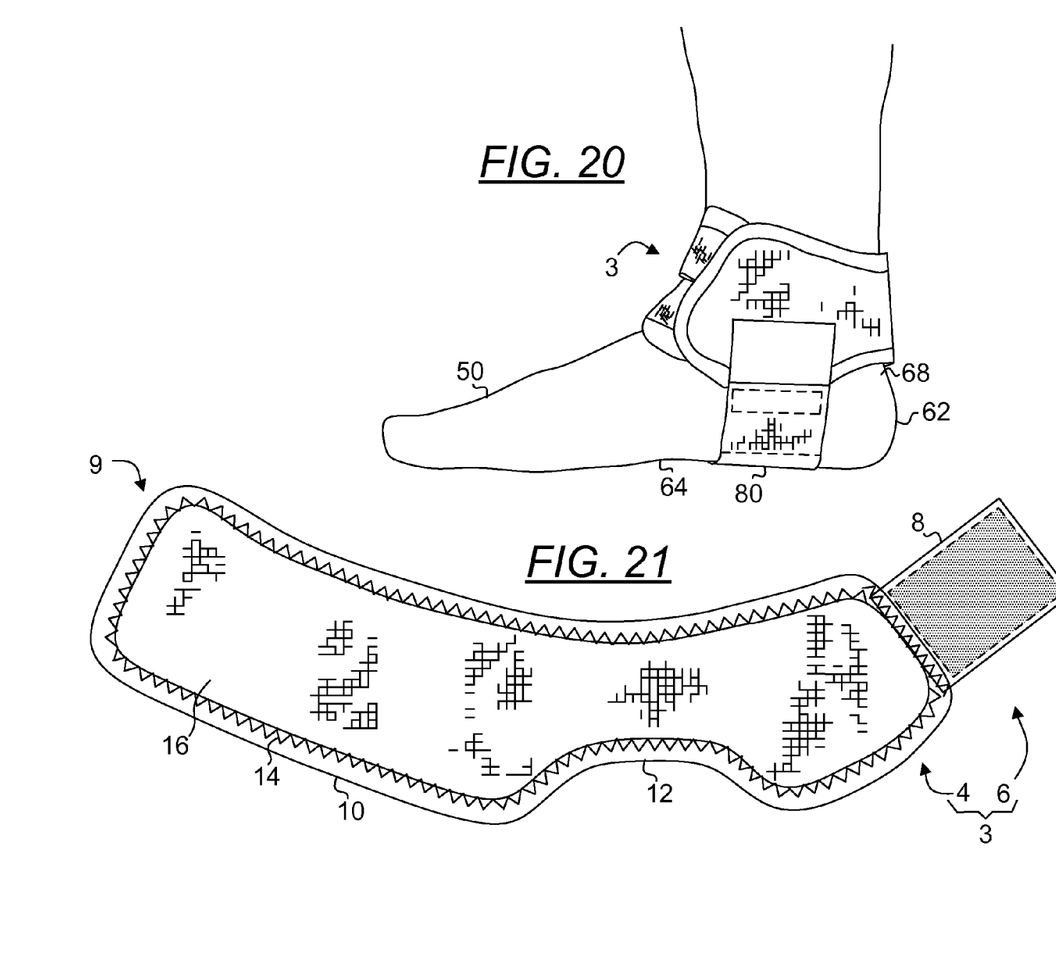
FIG. 20 is a view of a second embodiment of the present plantar strap assembly disposed on a foot, depicting the solution the present plantar strap assembly offers to solve problems associated with a conventional plantar strap assembly.
FIG. 21 is a front orthogonal view of a second embodiment of an ankle strap.

FIG. 20 is a view of a second embodiment of a present plantar strap assembly disposed on a foot, depicting the solution the present plantar strap assembly offers to solve problems associated with a conventional plantar strap assembly. In contrast to the conditions shown in FIGS. 18 and 19, the present plantar strap assembly 80 is sufficiently wide such that a user does not need to decide between disposing the strap assembly 80 forwardly or rearwardly as it is sufficiently wide to encompass a good portion of the plantar fascia. The ankle strap 3 is sufficiently sturdy to serve as anchoring points for strap assembly 80.

FIG. 21 is a front orthogonal view of a second embodiment of an ankle strap. In this embodiment, only one hook strap 8 is used. For circumstances where the possibility of the band 4 unfurling under normal use is non-existent, only one hook strap 8 is required to secure the ankle strap 3 to the ankle while serving as anchor points for a plantar strap assembly 30, 80.

The detailed description refers to the accompanying drawings that show, by way of illustration, specific aspects and embodiments in which the present disclosed embodiments may be practiced. These embodiments are described in sufficient detail to enable those skilled in the art to practice aspects of the present invention. Other embodiments may be utilized, and changes may be made without departing from the scope of the disclosed embodiments. The various embodiments can be combined with one or more other embodiments to form new embodiments. The detailed description is, therefore, not to be taken in a limiting sense, and the scope of the present invention is defined only by the appended claims, with the full scope of equivalents to which they may be entitled. It will be appreciated by those of ordinary skill in the art that any arrangement that is calculated to achieve the same purpose may be substituted for the specific embodiments shown. This application is intended to cover any adaptations or variations of embodiments of the present invention. It is to be understood that the above description is intended to be illustrative, and not restrictive, and that the phraseology or terminology employed herein is for the purpose of description and not of limitation. Combinations of the above embodiments and other embodiments will be apparent to those of skill in the art upon studying the above description. The scope of the present disclosed embodiments includes any other applications in which embodiments of the above structures and fabrication methods are used. The scope of the embodiments should be determined with reference to the appended claims, along with the full scope of equivalents to which such claims are entitled.

We claim:

1. A foot ailment support and cushion apparatus configured for supporting an ankle and a plantar fascia of a foot, said apparatus comprising:
    (a) an ankle strap comprising:
        (i) a generally curvilinear band having an inner surface, an outer surface, two first longitudinal ends, a minor edge, a major edge, a length, a width and a notch, wherein said inner surface is opposingly disposed from said outer surface, said minor edge connects to said major edge at said two first longitudinal ends of said curvilinear band and said notch is disposed along a portion of said major edge, each of said major and minor edges is curvilinear when one of said inner surface and said outer surface is laid flat and said width is substantially constant along said length of said generally curvilinear band except said portion of said major edge on which said notch is disposed; and
        (ii) an attaching means disposed on one of said two first longitudinal ends; and
    (b) a detachable and re-attachable discrete plantar strap assembly having two attachment ends and an elastic strap,
wherein said curvilinear band is configured to be wrappable around the ankle such that said attaching means is removably secured to said outer surface and a shape of a deployed form of said curvilinear band conforms to the shape of the ankle, said plantar strap assembly is configured to be disposed such that said elastic strap is disposed along a medial aspect of a plantar fascia of the foot and each of said two attachment ends is removably attached to a portion of said outer surface of said curvilinear band such that a pressure applied on the plantar fascia is adjustable by altering the location on said outer surface of said curvilinear band to which at least one of said two attachment ends is attached.

2. The apparatus of claim 1, wherein said width of said elastic strap is about 2 inches.

3. The apparatus of claim 1, wherein said attaching means comprises more than one hook strap extending outwardly from said one of said two first longitudinal ends.

4. The apparatus of claim 1, further comprising a gelatin pack disposed around at least a portion of said notch, wherein said notch is configured for engaging the Achilles tendon region of the foot and said gelatin pack comprises at least two gelatin-filled compartments.

5. The apparatus of claim 1, wherein each said attachment end is fabricated of a material having micro hooks.

6. The apparatus of claim 1, wherein said outer surface comprises loops configured for engagement with hooks such that inadvertent engagement of said outer surface with unintended materials is avoided.

7. The apparatus of claim 1, wherein said inner surface is a breathable washable antimicrobial moisture wicking mesh material selected from the group consisting of polyester and nylon.

8. The apparatus of claim 1, wherein said outer surface is configured for removable engagement with said attaching means and said two attachment ends and said outer surface is fabricated of a material selected from the group consisting of polyester and nylon.

9. A foot ailment support and cushion apparatus configured for supporting an ankle and a plantar fascia of a foot, said apparatus comprising:
    (a) an ankle strap comprising:
        (i) a generally curvilinear band having an inner surface, an outer surface, two first longitudinal ends, a minor edge, a major edge, a length, a width and a notch, wherein said inner surface is opposingly disposed from said outer surface, said minor edge connects to said major edge at said two first longitudinal ends of said curvilinear band and said notch is disposed along a portion of said major edge, each of said major and minor edges is curvilinear when one of said inner surface and said outer surface is laid flat and said width is substantially constant along said length of said generally curvilinear band except said portion of said major edge on which said notch is disposed; and
        (ii) an attaching means disposed on one of said two first longitudinal ends; and
    (b) a detachable and re-attachable discrete plantar strap assembly having two attachment ends and an elastic strap, wherein each said attachment end is fabricated of a material having micro hooks,
wherein said curvilinear band is configured to be wrappable around the ankle such that said attaching means is removably secured to said outer surface and a shape of a deployed form of said curvilinear band conforms to the shape of the ankle, said plantar strap assembly is configured to be disposed such that said elastic strap is disposed along a medial aspect of a plantar fascia of the foot and each of said two attachment ends is removably attached to a portion of said outer surface of said curvilinear band such that a pressure applied on the plantar fascia is adjustable by altering the location on said outer surface of said curvilinear band to which at least one of said two attachment ends is attached.

10. The apparatus of claim 9, wherein said width of said elastic strap is about 2 inches.

11. The apparatus of claim 9, wherein said attaching means comprises more than one hook strap extending outwardly from said one of said two first longitudinal ends.

12. The apparatus of claim 9, further comprising a gelatin pack disposed around at least a portion of said notch, wherein said notch is configured for engaging the Achilles tendon region of the foot and said gelatin pack comprises at least two gelatin-filled compartments.

13. The apparatus of claim 9, wherein said outer surface comprises loops configured for engagement with hooks such that inadvertent engagement of said outer surface with unintended materials is avoided.

14. The apparatus of claim 9, wherein said inner surface is a breathable washable antimicrobial and moisture wicking mesh material selected from the group consisting of polyester and nylon.

15. The apparatus of claim 9, wherein said outer surface is configured for removable engagement with said attaching means and said two attachment ends and said outer surface is fabricated of a material selected from the group consisting of polyester and nylon.

* * * * *